United States Patent
Comstock et al.

[11] Patent Number: 5,985,395
[45] Date of Patent: Nov. 16, 1999

[54] SURGICAL INCISE DRAPE

[75] Inventors: Kristen L. Comstock, Minneapolis; Matthew T. Scholz; Gregg A. Patnode, both of Woodbury, all of Minn.; Robert A. Asmus, Hudson, Wis.; Charles L. Newman, Stillwater, Minn.; Nancy E. Stewart, Afton, Minn.; Thomas L. Agrimson, Woodbury, Minn.

[73] Assignee: 3M Innovative Properties Company, St. Paul, Minn.

[21] Appl. No.: 08/857,723

[22] Filed: May 16, 1997

Related U.S. Application Data

[63] Continuation-in-part of application No. 08/648,786, May 16, 1996, abandoned.

[51] Int. Cl.⁶ .................................................. A61B 19/08
[52] U.S. Cl. .................. 428/40.1; 128/855; 206/440; 428/41.7; 428/41.8; 428/42.2; 428/121; 428/192; 602/52; 602/54; 602/57; 602/58
[58] Field of Search ................. 428/40.1, 192, 428/41.7, 41.8, 42.2, 121; 602/52, 54, 57, 58; 128/855; 206/440

[56] References Cited

U.S. PATENT DOCUMENTS

| | | | |
|---|---|---|---|
| Re. 31,886 | 5/1985 | Hodgson | 428/40 |
| Re. 31,887 | 5/1985 | Hodgson | 428/355 |
| 3,878,843 | 4/1975 | Morgan | 128/132 |
| 4,051,845 | 10/1977 | Collins | 128/855 |
| 4,310,509 | 1/1982 | Berglund et al. | 424/28 |
| 4,323,557 | 4/1982 | Rosso et al. | 425/28 |
| 4,452,845 | 6/1984 | Lloyd et al. | 428/220 |
| 4,513,739 | 4/1985 | Johns | 128/156 |
| 4,596,244 | 6/1986 | Jackson | 128/855 |
| 4,598,004 | 7/1986 | Heinecke | 428/40 |
| 4,614,183 | 9/1986 | McCracken | 602/57 |
| 4,627,427 | 12/1986 | Arco | 128/855 |
| 4,701,509 | 10/1987 | Sun et al. | 526/264 |
| 4,732,808 | 3/1988 | Krampe et al. | 428/355 |
| 4,744,355 | 5/1988 | Faasse, Jr. | 128/156 |
| 4,753,232 | 6/1988 | Ward | 128/156 |
| 4,798,201 | 1/1989 | Rawlings et al. | 128/156 |
| 4,832,008 | 5/1989 | Gilman | 128/155 |
| 4,846,164 | 7/1989 | Martz | 128/155 |

(List continued on next page.)

FOREIGN PATENT DOCUMENTS

| | | |
|---|---|---|
| 607504 | 10/1960 | Canada ..................................... 602/57 |
| 0 120 840 | 10/1984 | European Pat. Off. . |
| 2 131 299 | 6/1984 | United Kingdom . |
| 2239181 | 6/1991 | United Kingdom . |
| WO 84/01285 | 4/1984 | WIPO . |
| WO 89/01345 | 2/1989 | WIPO . |

OTHER PUBLICATIONS

Hager, K.S., Treston Aurand, J. "A Comparison of Two Skin Preps Used in Cardiac Surgical Procedures"; AORN Journal, vol. 62, No. 3, Sep. 1995.

Sample of "Steri–Drape™ 1000 Towel Drape"; 3M.

Sample of "Steri–Drape™ 1010 Towel Drape"; 3M.

ASTM D4032–92 Standard Test Method for Stiffness of Fabric by the Circular Bend Procedure.

*Primary Examiner*—Nasser Ahmad
*Attorney, Agent, or Firm*—Stephen W. Bauer; Kevin W. Raasch; Eloise J. Maki

[57] ABSTRACT

An incise drape suitable for use in surgical procedures. The drape comprises a substantially transparent flexible film that has at least a portion of one major surface coated or covered with a pressure sensitive adhesive, and a two liners removably covering the adhesive. Each liner has a handle spaced from the opposite side edges of the film, and a body portion attached to the handle. The body portion of each liner extends along the adhesive from handle in the direction away from the other liner. The drape is repeatedly folded over from the opposite side edges of the film toward the handles so that the drape may be unfolded and the adhesive exposed by pulling the handles apart.

42 Claims, 9 Drawing Sheets

U.S. PATENT DOCUMENTS

| | | | |
|---|---|---|---|
| 4,931,282 | 6/1990 | Asmus et al. | 424/448 |
| 5,017,625 | 5/1991 | Ansell | 521/159 |
| 5,061,258 | 10/1991 | Martz | 604/307 |
| 5,153,040 | 10/1992 | Faasse, Jr. | 428/40 |
| 5,156,911 | 10/1992 | Stewart | 428/355 |
| 5,204,110 | 4/1993 | Cartmell et al. | 424/443 |
| 5,290,615 | 3/1994 | Tushaus et al. | 428/40 |
| 5,593,395 | 1/1997 | Martz | 604/304 |
| 5,633,070 | 5/1997 | Murayama et al. | 428/194 |

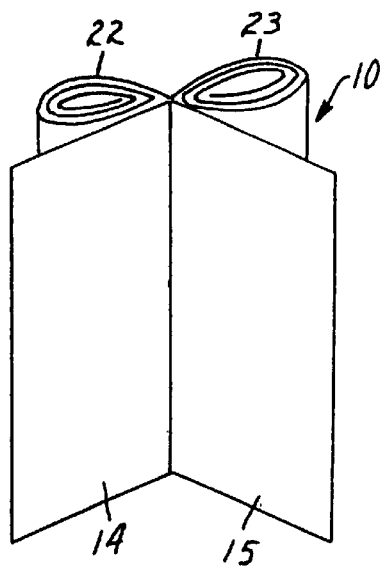
Fig. 4
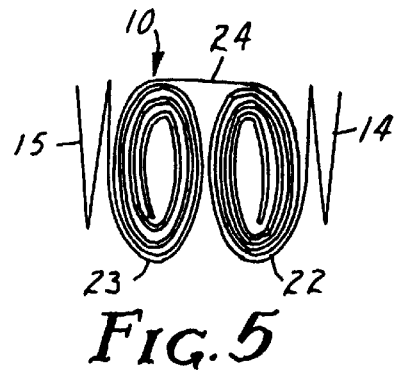
Fig. 5
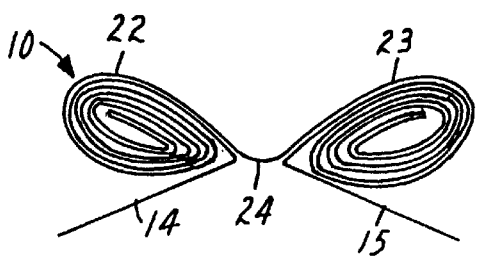
Fig. 6
Fig. 14
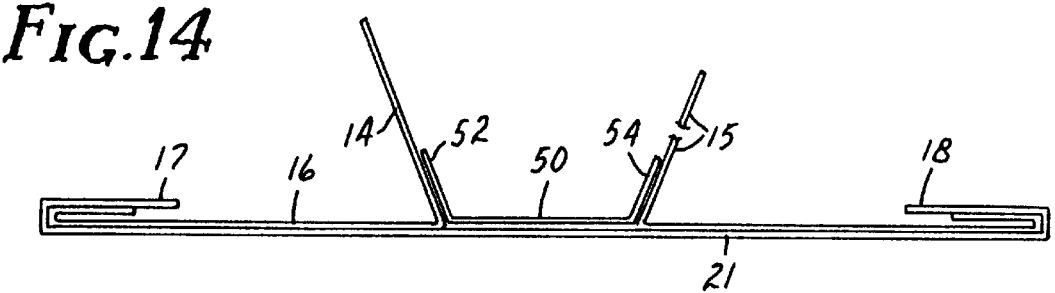
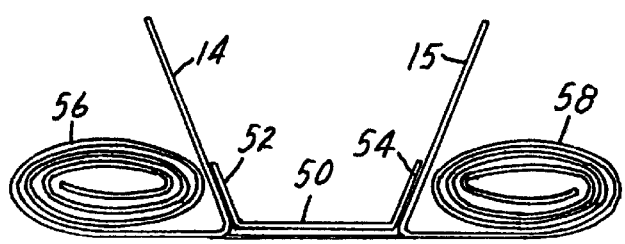
Fig. 15
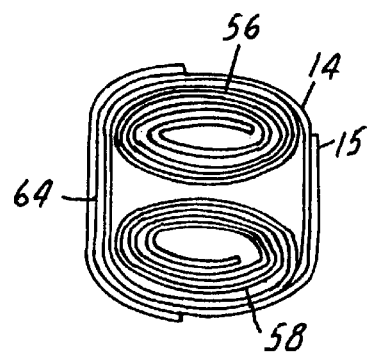
Fig. 16

SURGICAL INCISE DRAPE

This application is a continuation-in-part of U.S. patent application Ser. No. 08/648,786, filed May 16, 1996, now abandoned.

FIELD OF THE INVENTION

This invention relates to an incise drape suitable for use in surgical procedures.

BACKGROUND OF THE INVENTION

Many of today's surgical procedures involve the use of an incise drape. The incise material is usually a clear polymeric film with an adhesive on one side which is in turn covered with a release liner. Two suppliers of incise material are the Minnesota Mining and Manufacturing Company, St. Paul, Minn., USA and T. J. Smith and Nephew Ltd., Examples of incise material can be found in U.S. Pat. Nos. 4,310,509; 4,323,557; 4,452,845; Re. 31,886 and Re. 31,887.

Most typically, incise material is used in connection with towels or surgical drapes to maintain the surgical area as clean and sterile as possible to help reduce the risk of infection. Once the surgical area of the patient has been scrubbed and treated with a antimicrobial, the surgical site is squared-off by the use of sterile towels and a surgical drape which has a fenestration of a size which is larger than the expected size of the incision. An incise material is then used to cover all or a portion of the patient's skin left exposed by the towels or the fenestration in the surgical drape or mainsheet.

One purpose in using the incise material is to help reduce the migration of germs and bacteria into the incision site. This is because, despite the cleansing of the skin, the pores still contain additional germs and bacteria which can migrate to the surface as the skin is moved and worked during the course of the surgical procedure. By covering the skin with incise material, it has been found that a lower incidence of surgical site contamination occurs.

Common practice is to take the sterile incise drape out of a disposable, protective bag (e.g., made from polyethylene) and deliver it to the sterile field in an aseptic manner. The drape typically comes in sizes as small as 13×18 cm (5×7 inches) but are usually 40×30 cm (16×12 inches) up through 90×120 cm (36×48 inches) and larger. Conventional surgical drapes usually consist of an antimicrobial film incise material covered by a one-piece silicone coated paper release liner with equal dimensions to the film so that the adhesive is protected.

Typical practice is for two people to stand on opposite sides of the operating table, each within the sterile field with sterile gloved hands. One person grips the handle portion of the drape (a 10 to 15 cm film margin free of adhesive) while the other person takes the paper liner and pulls it away from the underside exposing the adhesive. The drape is then applied to the patient at the surgical site and subsequently smoothed out and pressed onto the patient with a sterile towel. With larger drapes, this might require three or more people.

Current incise drapes are usually large and cumbersome to apply to the patient without wrinkles and without the drape sticking to itself in the process. As described above, drape application usually requires two or three people, creating a drain on operating room personnel and contributing to rising hospital costs. Applying conventional incise drapes can be a frustrating experience, even for those skilled in the art of applying incise drapes. The drape is flimsy (so as to be very conformable to the contours of the skin) with an aggressive pressure sensitive adhesive for adhesion to the skin. These two quality characteristics, when combined with the large size of incise drapes, frequently results in the application of a wrinkled drape.

It is imperative that the incise drape be wrinkle-free after it is applied, especially directly at the incision point in order for the surgeon to be able to make a clean surgical incision. Wrinkles in the drape make it difficult for the surgeon to see through to the skin (translucency and visibility are important) and, more importantly, wrinkles may not contain the bacteria on the skin as well as they should. Maintaining a sterile surface at the point of incision helps prevent surgical wound infections. Hager, K. S.; Treston Aurand, J. "A Comparison of Two Skin Preps Used in Cardiac Surgical Procedures," AORN Journal, Vol. 62, No. 3, September 1995.

See, also, U.S. Pat. Nos. 4,513,739 and 4,598,004, and British Patent No. 2,131,299, which disclose applying a dressing center first to a wound.

SUMMARY OF THE INVENTION

This invention provides an incise drape that can be effectively applied to the patient by one person in wrinkle-free form so as to minimize the chance of infection and improve the visibility through the film. The incise drape is designed to improve utilization of operating room personnel, one of the costliest areas of the hospital. Additionally, the surgical incise drape is easy to apply and conforms to various contours of the patient's skin. Further, an aspect of the present invention is the manner in which the drape is folded to facilitate application using aseptic technique.

Generally, a surgical incise drape of the invention comprises a substantially transparent flexible film having opposite major surfaces and opposite side edges, a pressure sensitive adhesive on at least a portion of one of the major surfaces of the film, and two liners. Each liner has a handle spaced from the opposite side edges of the film, and a body portion attached to the handle and removably covering at least a portion of the adhesive. The body portion of each liner extends along the adhesive from handle in the direction away from the other liner. The drape is repeatedly folded over from the opposite side edges of the film towards the handles so that the drape may be unfolded and the adhesive exposed by pulling the handles apart.

For example, the drape may be repeatedly folded over by rolling the drape inwardly from the opposite side edges of the film, or by fan-folding the drape inwardly from the opposite side edges of the film.

This invention also provides a method of applying the multi-liner incise drape comprising the steps of a) pulling upon at least one of the handles to remove at least a portion of the liner and expose underlying adhesive;

b) placing the exposed adhesive portion upon the patient at the desired location;

c) pulling on the handles of all the liners simultaneously or sequentially to expose underlying adhesive; and d) smoothing down upon the patient the adhesive portions exposed due to step c) until the incise drape is properly applied.

Applicants have discovered that the incise drapes of this invention, which utilize two or more release liner pieces, greatly facilitate the application of the surgical drape by 1) reducing the number of persons required to apply the drape (normally one), 2) reducing the amount of drape wrinkling that occurs during application and 3) improving aseptic practice by reducing the time the adhesive portion of the drape is exposed to the environment during application.

BRIEF DESCRIPTION OF THE DRAWINGS

FIG. 4 is a plan view of the embodiment shown in FIG. 1 in substantially folded form.

FIG. 5 is a side view of the embodiment shown in FIG. 1 in completely folded form.

FIG. 6 is a side view of the embodiment shown in FIG. 4, inverted, immediately before application.

FIG. 14 is a side view of a fourth embodiment of the present invention, partially folded.

FIG. 15 is a side view of the embodiment shown in FIG. 14 but further rolled or folded.

FIG. 16 is a side view of the embodiment shown in FIG. 14, fully folded before packaging.

DETAILED DESCRIPTION OF PREFERRED EMBODIMENTS

Figure 1:
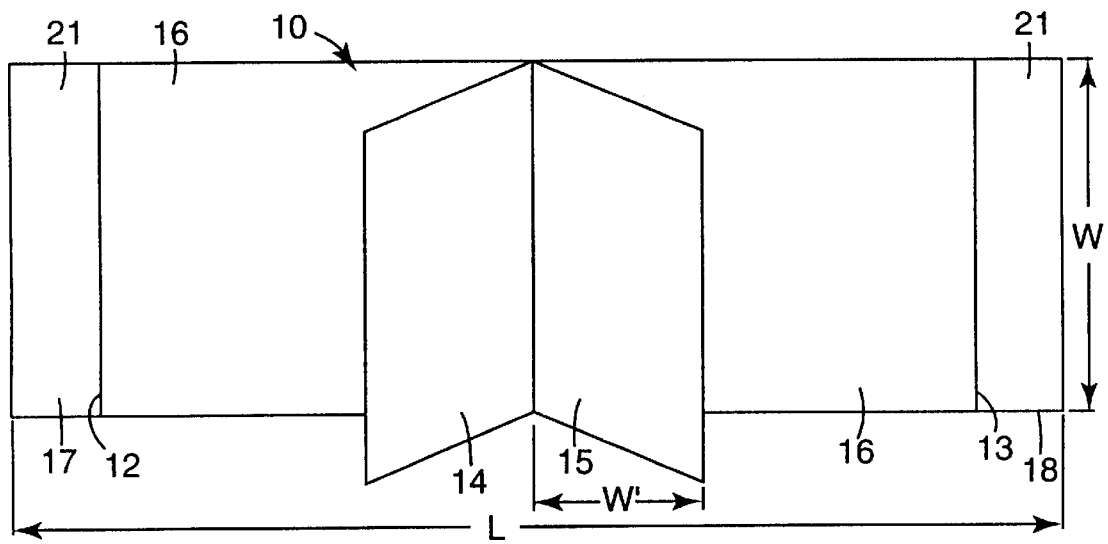
FIG. 1 is a plan view of a first embodiment of the present invention.
Figure 2:
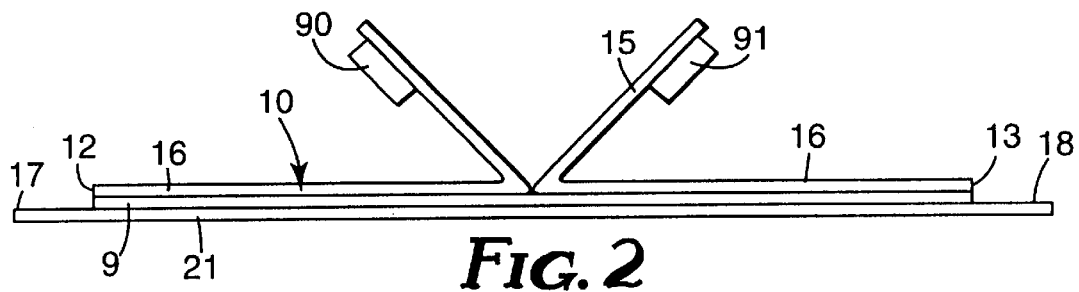
FIG. 2 is a side view of the embodiment shown in FIG. 1.
Figure 3:
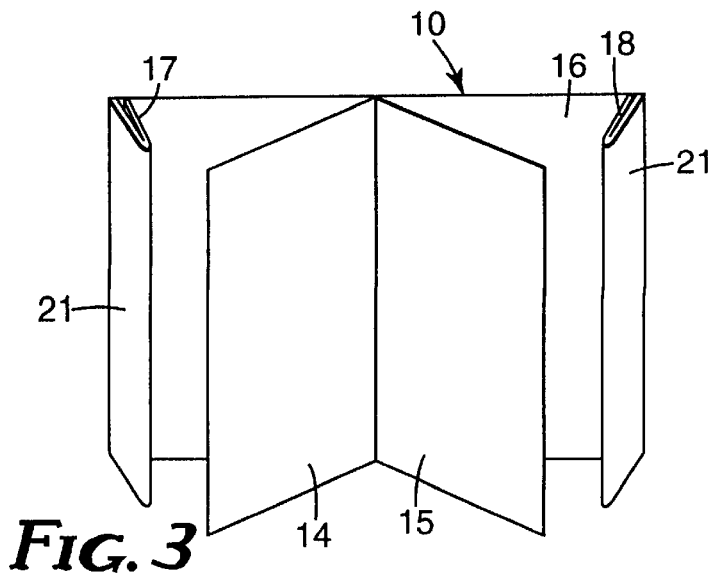
FIG. 3 is a plan view of the embodiment shown in FIG. 1, partially folded.
Figure 7:
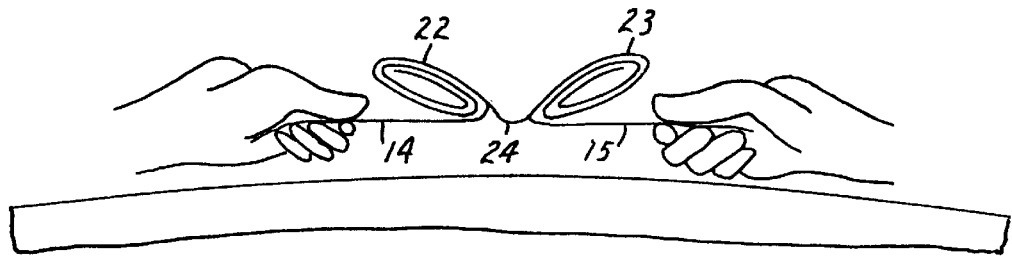
FIGS. 7–9 are side views of the first embodiment during stages of application to a patient.
Figure 8:
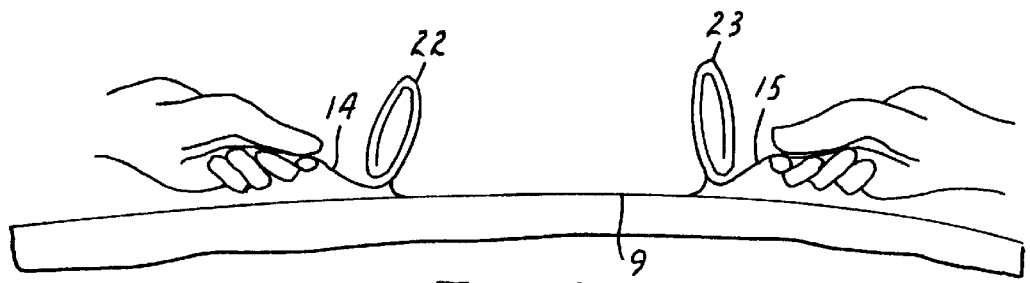
Figure 9:
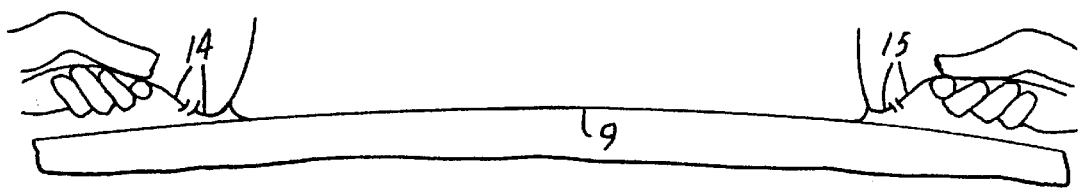
Figure 10:
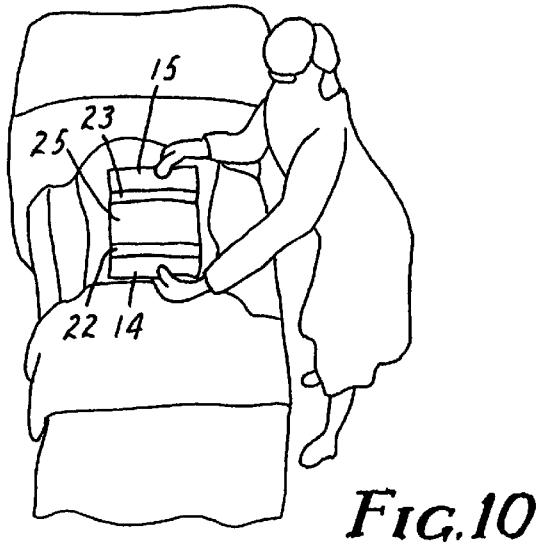
FIG. 10 is a perspective view of the embodiment shown in FIG. 9.

With particular reference to FIG. 1 it may be seen that an improved incise drape 10 of the present invention may be of generally rectangular configuration having, for example, a width (W) of 10 to 100 cm and a length (L) of 15 to 120 cm. The incise drape before folding, as illustrated in FIGS. 1 and 2, includes film 21 having a pressure sensitive adhesive portion 9 that is covered by multiple release liners 16.

Each release liner is provided with a handle portion 14, 15. While each release liner 16 is shown as being of equal length, the liners could easily differ in length depending upon the ultimate use of the drape. Preferably, however, the liners do not differ in length by more than 200 percent, and preferably by not more than 100 percent. While FIG. 1 illustrates the liners 16 abutting with the split between them perpendicular to the longitudinal axis or length of the drape (i.e., at a 90 degree angle to the length of the drape (L)), it is understood that the split between the liners could be at any angle from about 20–90 degrees from the length of the drape. Furthermore, the edge of the handles in contact with the adhesive need not be linear but could be in a sinusoidal or other arrangement.

Extending from the outer edges of the adhesive portion 9 of the film are optional tabs 17, 18. The tabs 17, 18 are useful for removing the drape from the patient after application. The tabs 17, 18 are most conveniently extensions of the film 21 which are not covered or coated adhesive. While the tabs 17, 18 are depicted along the width (W) of the drape at the outer edges, in an alternative embodiment the tabs 17, 18 could be located along the length (L) of the drape at the outer edges.

Alternatively, the tabs may also consist of separate materials bonded to the film. For example, the tabs may be bonded to the opposite side edges 12 and 13 of the film 21, and may be formed of plastic films (e.g., polyolefins, polyesters or polyamides), nonwoven sheets, knits, wovens, paper and coated paper sheets, as well as laminates of these materials.

The tabs 17 and 18 serve to be manually grasped to facilitate removing the drape from the patient after the procedure is completed and thus remain attached to the drape during the procedure. To prevent them from obstructing the surgical procedure, the tabs 17 and 18 are preferably highly conformable. The tabs 17 and 18, however, may be stiffened by forming the tabs of stiffer materials or by releasably attaching a stiffening strip (e.g., paper or coated paper) to an extension of the film that is not covered or coated with adhesive. Such a stiffening strip may be releasably attached to the film extension using an adhesive, perforation or peelable thermal bond.

While the drape depicted in FIGS. 1 and 2 includes tabs 17 and 18, the release liners 16 can alternatively function as tabs 17 and 18. In this embodiment (shown in FIGS. 11 and 12) at least a portion of release liners 16, after separation from the adhesive portion 9 of the film (as described below), remain attached to the peripheral ends 12 and 13 at each opposite end of the adhesive portion 9.

The handles 14 and 15 are preferably at least 5 cm in width (W'), more preferably at least 7 cm, and most preferably 10 cm or more in order to protect the gloved hands of the applier from inadvertent contact with unsterile patient's skin (a violation of aseptic technique). These handles could be further extended to enable wrapping around the leg or arm. For this application the handles are preferable 20 to 30 cm in width, or larger. In use the liners would be wrapped around the limb and pulled with even tension allowing the incise portion of the drape to be applied to the skin. The handles 14, 15, while shown as extensions of release liners 16, may alternatively be made from a separate piece of material which is adhesively, thermally, ultrasonically or otherwise bonded to the release liners 16. The tabs 17, 18, like the handles, may alternatively be made from a separate piece of material and bonded to the incise drape.

Alternatively, the handles may also be made from a separate piece of material bonded to the release liner. For example, the handles may be formed of paper, paper board, coated paper or paperboard, plastic or plastic coated paper, and may be bonded to the release liner by tape, adhesive, or thermal bond (e.g., heat and pressure, ultrasonic welding, etc.). Preferred papers have basis weights of 80–400 g/m$^2$, more preferably 100–300 g/m$^2$ and most preferably 150–225 g/m$^2$.

As illustrated in FIG. 2, the handles 14 and 15 are preferably extensions of the release liner 14 and 15 to which stiffening strips 90 or 91 are attached adjacent the free ends of the handles 14, 15. The stiffening strips 90 and 91 may be bonded to the handles 14 and 15 without extending beyond the handles as shown in FIG. 2, or may be bonded to the free ends of the handles so as to extend beyond the handles. Stiffening strips 90 and 91 help to keep the drape from wrinkling during application.

The stiffening strips 90 and 91 are desired when used with more conformable handles and liners, i.e. handles and liners that lack stiffness, for example, by having a stiffness of less than about 20 N and particularly those that have a stiffness of less than about 10 N as tested according to ASTM Test Method D4032-92 (Standard Test Method for Stiffness of Fabric by the Circular Bend Procedure), which is incorporated herein by reference. Examples of such conformable handles/liners include, for example, various thin polymeric film release liners having integral handle extensions. (As used herein, the term "integral" means that the handle extension and release liner form one continuous piece as opposed to separate pieces bonded together.) For handles having greater stiffness (e.g., greater than 20 N and particularly if greater than 30 N), the stiffening strip may be omitted but can still be used to provide greater assurance against wrinkling and also to serve as a rigid core facilitating packaging.

The folding of the drape 10 helps ensure wrinkle-free, and more importantly, aseptic delivery. Although many folding sequences are possible, the folding arrangements shown in FIGS. 3–6, 14–16 and 17–18 are preferred.

While the folding patterns illustrated in the figures are preferred, many folding patterns could be employed including for example, rolled, rolled and flattened, and fan-folded patterns. Desirable folding patterns allow the drape to be applied smoothly and yet not spontaneously unfold and drop onto the patient's skin, which might potentially compromise the sterility of the incise drape. The drape is folded upon itself many times from its edge in order to form a conveniently delivered package. The drape should be capable of maintaining the folded state either through proper fold pattern or by virtue of the stiffness of the liner, handles and/or tabs. This may preferably be accomplished by providing release liners having a sufficiently high modulus that they are able to maintain a crease.

Suitable liner materials include release coated plastics and paper products as well as paper/plastic laminates. Plastic films may alternatively be employed, for example, polyesters, or polyolefins having a thickness of at least about 2 mil (e.g., 2 mil high density polyethylene available from Rexam Release, Bedford Park, Ill., USA, as grade 102105 2 mil NT HDP A16/000) and most preferably at least 3 mil (e.g., 4 mil medium density polyethylene also available from Rexam Release. Polyolefin-coated papers may also be used.

One method manufacturing the incise drape involves coating an adhesive solvent solution onto the liner, removing the solvent in an oven, and subsequently laminating this adhesive-coated liner to the film backing. Since the solvent is removed typically at elevated temperature in an oven, certain low melting polymeric liners such as those made of low or medium density polyethylene may be adversely effected. And liners incorporating a higher melting polymer such as a polyester layer, which are able to withstand the elevated temperature during drying, are not very flexible and can be quite noisy during application. A preferred approach is to form film liners by laminating polymers with high melting points and polymers with low melting points.

Desirable high melting point polymers for the preferred laminated film are characterized by having a melt temperature in excess of about 175° C. and preferably in excess of about 190° C. (as listed in Modern Plastics Encyclopedia Vol. 66 no. 11, 1989, McGraw Hill). Polymers useful for this layer include but are not limited to polyester (e.g. polyethylene terephthalate, polybutylene terephthalate etc.), polyamides (e.g. nylon 6,6; nylon 6), cellulose acetate and the like. The high melting point polymer layer should generally be present in the laminate in a total thickness (i.e., the sum total of all layers) of at least about 6 microns, preferably at least 12 microns and most preferably at least about 25 microns.

Desirable low melting point polymers for the preferred laminated film are characterized by having a melt temperature below about 175° C. and preferably below about 150° C.). Polymers useful for this layer include but are not limited to polyolefins (e.g., polyethylene, polypropylene, polybutylene, ethylene/vinyl acetate, ethylene methylacrylate and the like). The low melting point polymer layer should generally be present in the laminate in a total thickness (i.e., the sum total of all layers) of at least about 12 microns, preferably at least 25 microns and most preferably at least about 50 microns.

The preferred laminated film may be formed of two or more layers. For example, a high melting point polymer layer may be laminated on one or both sides by a low melting point polymer. In this manner, the high melting point polymer layer is able to support the stresses imparted in the drying oven while the low melting point polymer layer provides flexibility.

These laminated films may be formed by laminating premade films formed by an suitable method such as cast or blown extrusion. Alternatively, the laminates may be formed by coextrusion or extrusion lamination techniques.

Referring now to FIGS. 3–6, the tabs 17 and 18 are first folded over onto the release liner 16 from opposite ends of the drape, and then each tab 17 and 18 is rolled or folded over upon itself inwardly toward handles 14 and 15, respectively, to form folded sections 22 and 23. These sections 22 and 23 are further folded or rolled inwardly so that they lie on top of handles 14 and 15, respectively. In this manner central adhesive portion 24 is protected from wrinkling or otherwise adhering to additional packaging material. This central adhesive portion 24 is the first portion of the drape applied to the patient. Any portions of the handles 14, 15 that extend beyond sections 22 and 23 may be folded back over the exterior of sections 22 and 23 to facilitate easy access to the handles during application. The entire folded drape may then be flattened, if desired, and placed in an outer wrapper ready for sterilization. Suitable sterilization may be accomplished by gamma irradiation, electron beam, steam, or cold sterilization methods such as ethylene oxide, hydrogen peroxide and the like.

The drape thusly folded is ready for easy wrinkle-free, aseptic delivery to the patient by preferably one person. When ready to apply to the patient, in a preferred method the drape is inverted as shown in FIG. 6 and the central adhesive portion 24 is exposed for the first time. As shown in FIGS.

7–10, the person applying the drape will take handles 14 and 15 in opposite hands, pull slightly on each handle to expose central adhesive portion 24, place the adhesive portion 24 on the patient at the desired site, and continue pulling on handles 14 and 15 until the entire adhesive portion 9 is applied to the patient, smoothing the drape down as liners 16 are being released. Alternatively, after placing adhesive portion 24 on the patient, one handle may be completely removed before removing the second handle. In yet another alternative, the drape could be applied by two people each pulling on separate handles.

Release liners 16, after separation from adhesive portion 9 may be separated from the drape or at least a portion may remain attached to the drape at edges 12 and 13. If separated, release liner portions 16 may be discarded or utilized elsewhere in the procedure as described below.

Figure 11:
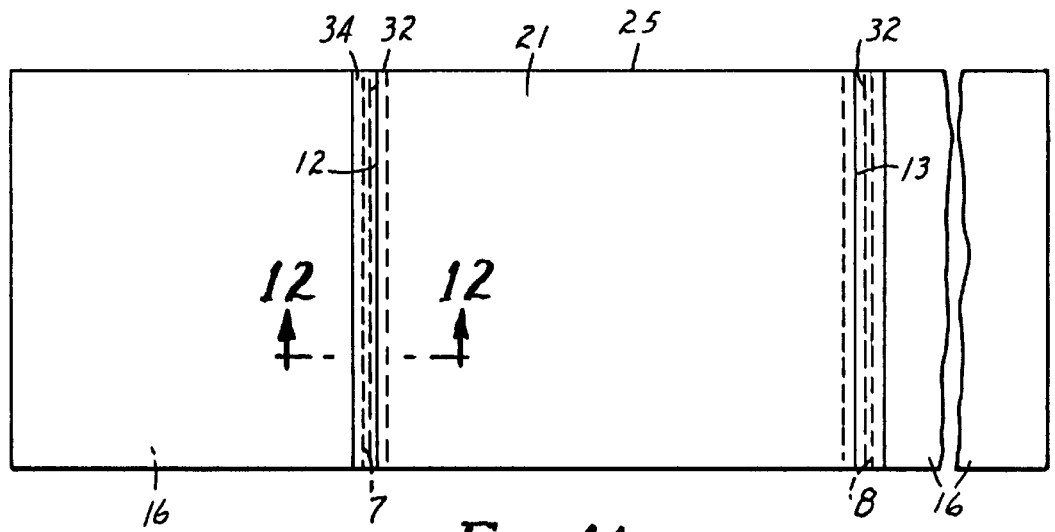
FIG. 11 is a plan view of a second embodiment of the present invention.

FIG. 11 illustrates the drape after application with release liners 16 still attached to the outer periphery of the film shown in FIG. 2. Adhesive portion 9 in combination with film 21 (shown in FIG. 2) forms the incise portion 25 of the drape. In this embodiment, the liners 16 may serve as tabs for removal of the drape, similar to tabs 17 and 18 depicted in FIG. 1, as well as providing further draping protection.

When release liners 16 are to be separated from the incise portion 25 of the drape and utilized elsewhere as part of the surgical procedure, adhesive sections 7 and 8 are provided at some location on one or more of the release liners 16. For example, as shown in FIG. 11, the adhesive sections 7 and 8 are located at the intersection between incise portion 25 and each release liner 16. Alternatively, the adhesive sections 7, 8 could be provided at any other part of the release liner, most conveniently near one edge.

The adhesive on each strip 7 and 8 may be protected by separate release liners, as is well known in the art. For example, the adhesive sections 7,8 could also be positioned beneath stiffening strips 90 and 91 (FIG. 2), thus serving to bond stiffening strips 90 and 91 to the liner while permitting the stiffening strips 90 and 91 to be removed to reveal adhesive sections 7,8. The adhesive sections 7,8 can then be used to adhere the liner at an alternate location. In this example, it is contemplated that the stiffening strips 90 and 91 would be provided with a release-coated surface to facilitate removal from the adhesive sections 7,8.

In use the liners 16 with adhesive portions 7, 8 are detached from incise drape portion 25 and applied using the adhesive portion at a second location, such as another position on the patient, surgical table, instrument which can eliminate other drapes currently used for this purpose. Preferably, when the liner is detached, a section of non-adhesive liner or drape material remains as a tab to remove the drape when surgery is complete.

Figure 12:
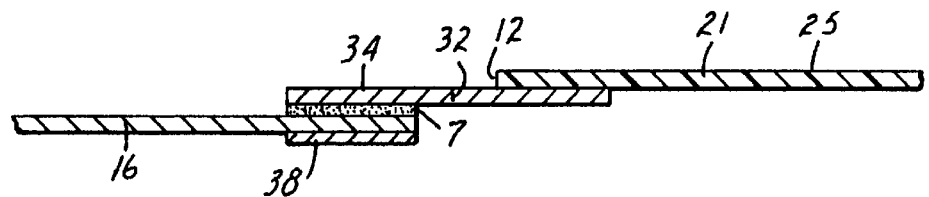
FIG. 12 is a partial sectional view taken along the line 12—12 of FIG. 11, showing attachment of the liners to the incise drape.

The liners 16 could be removed from incise portion 25 along perforations 32. An alternative embodiment of a detachable liner 16 is illustrated in FIG. 12. In this embodiment incise portion 25 is joined at either peripheral edge 12, 13 to liner 16 by a tab 34 and underlying adhesive portion 7. The underside of tab 34 has a low adhesion backsize (LAB) to facilitate removal of liner 16, with adhesive 7, from the rest of the drape 34. Optionally, as shown in FIG. 12, a reinforcement strip 38 is positioned on the underside of liner 16. Such a reinforcement strip rigidifies removed liner 16 to aid in wrinkle-free application at another location.

Figure 13:
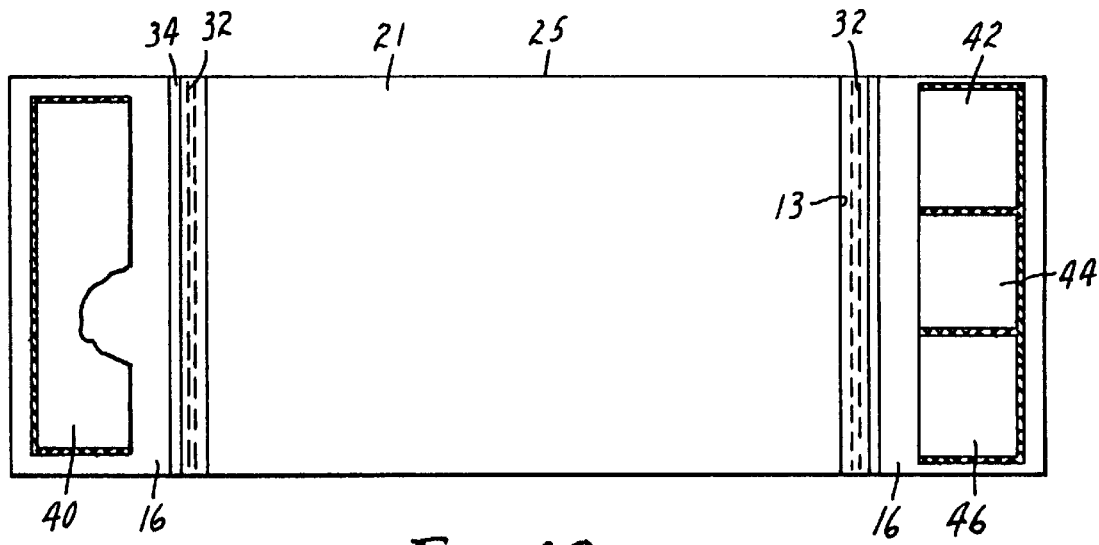
FIG. 13 is a plan view of a third embodiment of the present invention.

FIG. 13 illustrates a further embodiment of the present invention. In this embodiment a pouch 40 or multiple pouches 42, 44 and 46 are present on liner portions 16. Alternatively, or in addition, the liner portions 16 could include other attachments such as tubing organizers, cautery holsters, instrument holders, fluid collection pouches, etc. The pouches (40, 42, 44, 46) may be formed by sealing a piece of plastic film, paper, or textile cloth including wovens, knits and nonwovens, or laminates thereof, to the surface of the liner portion 16. Preferably a thermoplastic film is used. Sealing means include transfer adhesive, hot melt adhesive, double coated tape, heat sealing, ultrasonic sealing and the like. Preferably the pouches are formed by heat sealing a thermoplastic film directly to the liner on the side opposite the LAB. Alternatively, preformed pouches may be attached directly to liner portion 16. The three major edges of the pouch define an opening which for larger pouches may be used as a fluid collection means and for smaller pouches may be used for storage of the surgical supplies and instruments. The opening of the pouch so formed may further have a means for keeping the pouch "open" so that fluid may drain into the pouch. For example, a piece of reticulated foam may be used. Furthermore, the edge of the pouch defining the opening may be formed with the film folded back on itself to form a flap in opening the pouch and providing reinforcement to the opening. The pouch may also have a fitment to facilitate fluid drainage.

Another embodiment of the invention illustrated in FIG. 14 includes a smaller piece of release liner 50 in addition to the two larger liner portions 16. This third liner 50 would cover a portion near the center of the incise drape (where the drape will be initially applied). Release liner 50 has handles 52 and 54 on opposite edges to facilitate removal of liner 50 from the adhesive portion of the drape.

Referring to FIGS. 14, 15 and 16, this drape embodiment is folded before use, by first folding tabs 17 and 18 onto release liner 16, and rolling inward towards handles 14 and 15, respectively, to form folded sections 56 and 58. These sections 56 and 58 are then folded under liner 50, as shown in FIG. 16.

When ready for application, liner 50 is removed by grasping handles 52 or 54 to expose the underlying adhesive section 64. The drape is inverted and, because adhesive portion 64 is supported by folded portions 56 and 58, wrinkle-free application of adhesive portion 64 to the patient is facilitated. Drape application is completed by grasping handles 14 and 15 with opposite hands and pulling to expose the remaining adhesive portions under liners 16.

Figure 17:
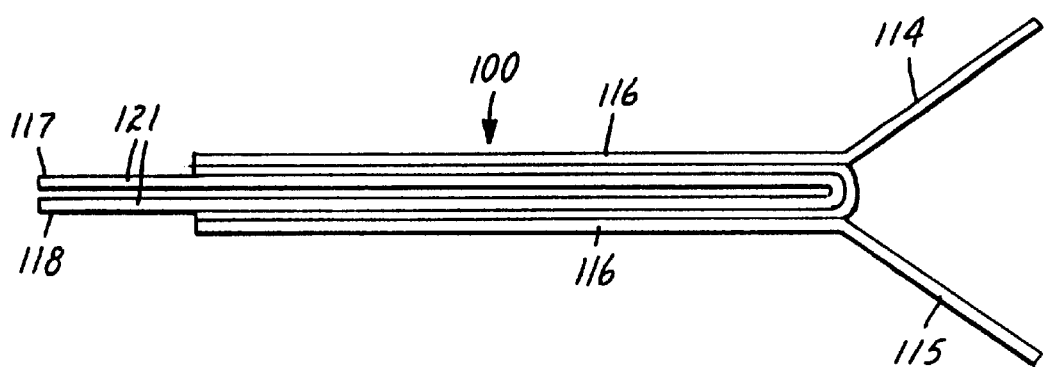
FIG. 17 is a side view of a fifth embodiment of the present invention, not to scale.
Figure 18:
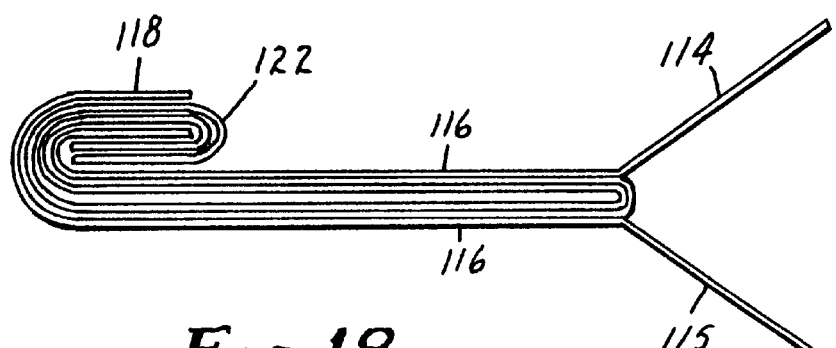
FIG. 18 is a side view of the embodiment shown in FIG. 17, partially rolled.

An alternative folding method is shown in FIGS. 17 and 18. The drape 100 (including film 121 and attached release liner portions 116) is first folded back upon itself, with film 121 abutting film 121, at the junction of handles 115 and 114. Optional tab portions 118 and 117 (which comprise uncoated film) are rolled together onto release liner 116, and rolling is continued towards handles 114 and 115, until a single rolled section 122 is formed. To apply, handles 114 and 115 are grasped in opposite hands and pulled to expose adhesive portion 124, which is then placed upon the patient as described above.

Figure 19:
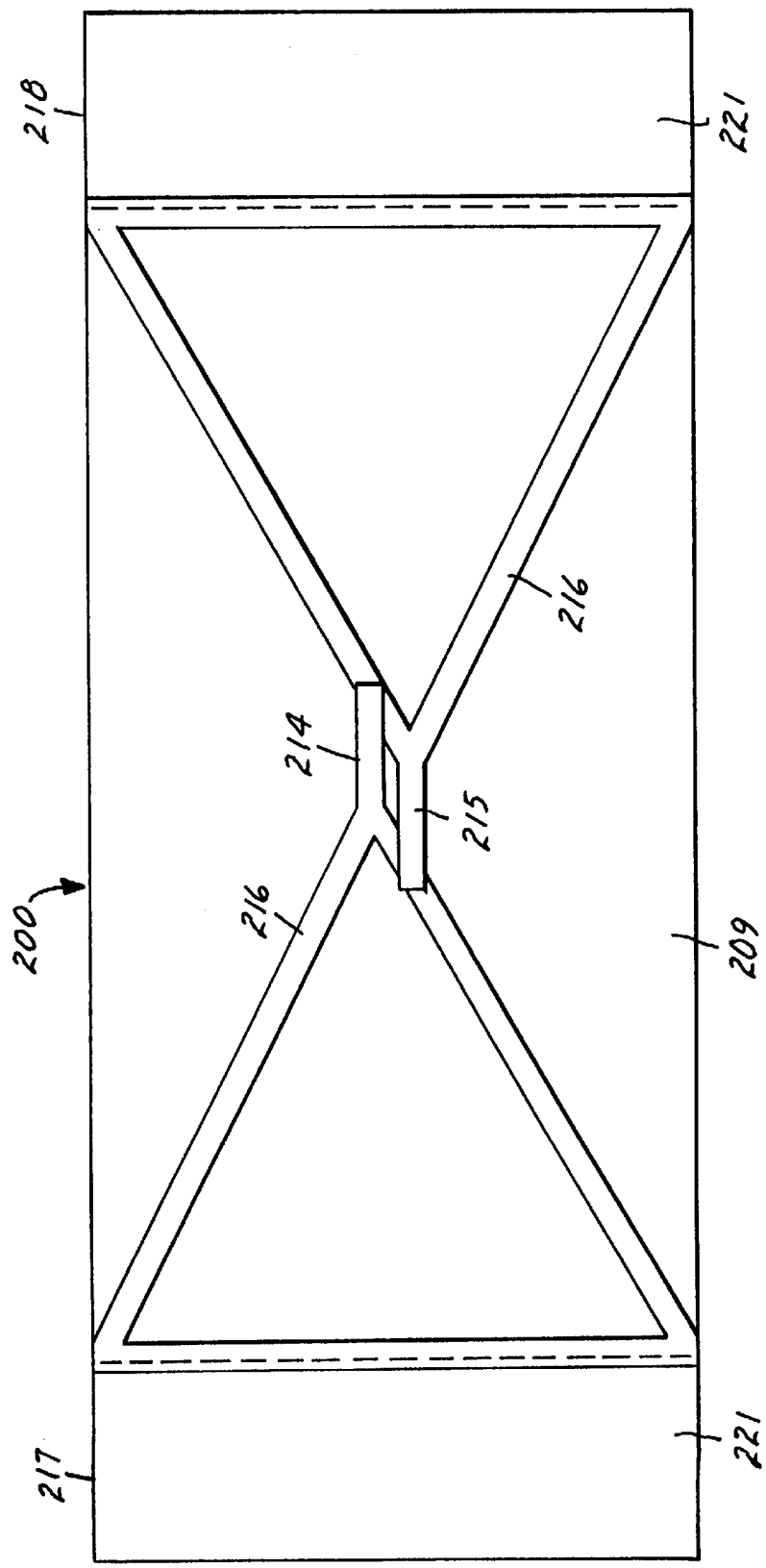
FIG. 19 is a plan view of a sixth embodiment of the present invention.
Figure 20:
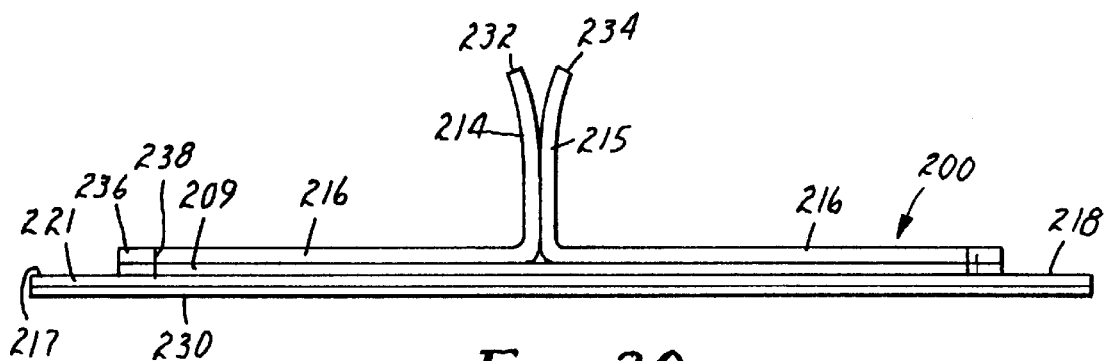
FIG. 20 is a side view of the embodiment shown in FIG. 19, not to scale.

FIGS. 19, 20, 21 and 22 illustrate another embodiment of this invention. FIG. 19 illustrates drape 200 in unfolded form. In this embodiment liners 216 cover only a portion of the adhesive portion 209 of the film 221. Each liner 216 has a handle 214 and 215. As shown in FIG. 20, each liner 216 is anchored at 236 to the adhesive portion 209. Liners 216 can be removed by perforation at 238, leaving the tabs created by 236. Tabs 217 and 218 at opposite ends of the adhesive portion 209 are preferably constructed from release liner materials described below.

Figure 21:
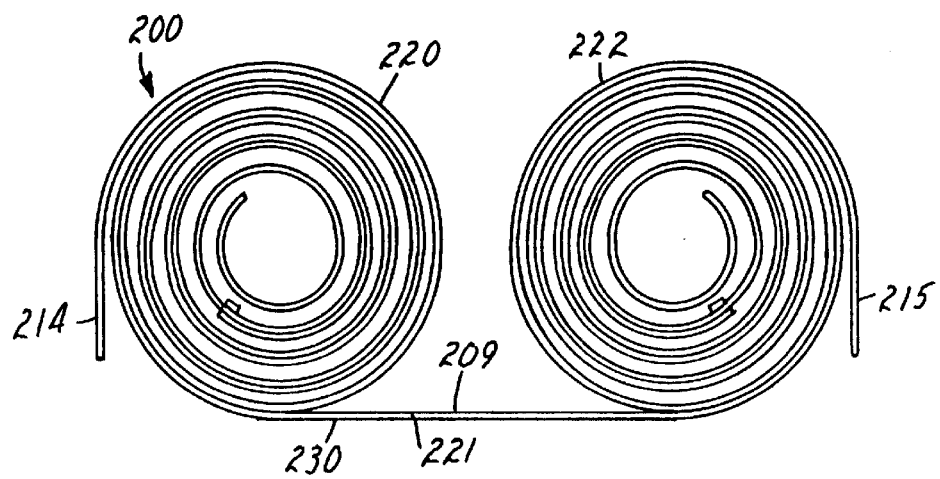
FIG. 21 is a side view of the embodiment shown in FIG. 19 in rolled form.

As shown in FIG. 21, tabs 217 and 218 are rolled in scroll form over liners 216 towards the center of the drape. As such, tabs 217 and 218 form cores 220 and 222, respectively, around which the drape 200 is wound. It is also possible to use conventional cylindrical cores comprised of cardboard, paperboard, plastic and the like to replace tabs 217 and 218. When using conventional cores, the core is preferably easily detachable from the incise drape after application. The core will typically have a diameter of less than 4 cm and preferably less than about 2.5 cm. Due to the rolling of the cores 220 and 222 over exposed adhesive portion 209, a low adhesion backsize (LAB) coating 230 is preferably applied to the non-adhesive side of film 221.

Figure 22:
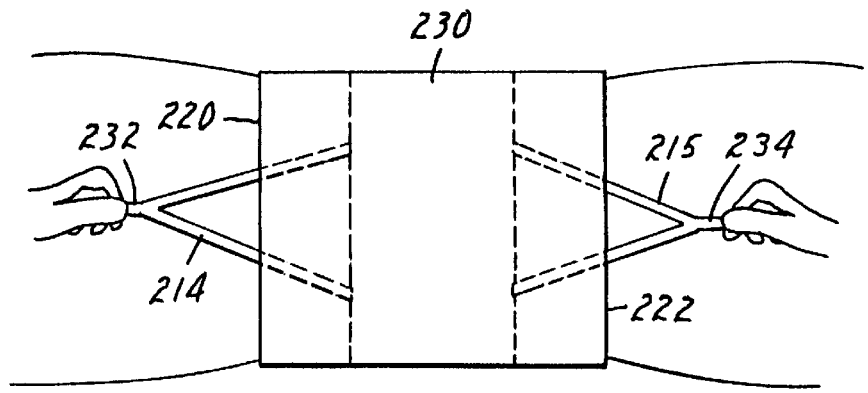
FIG. 22 is a plan view of the sixth embodiment partially unrolled.

To apply the drape, as shown on FIG. 22, the healthcare worker grasps each handle 214 and 215 at ends 232 and 234, respectively, and pulls to expose a portion of the adhesive portion 209. The adhesive surface is then applied to the patient at the desired location, and the clinician continues to pull on handles 214 and 215 until the entire adhesive portion 209 is applied to the patient.

The folded construction of the drapes of the invention (illustrated, for example, in FIG. 6) provides a drape that can be easily applied to the patient without concern of contaminating the outer surface of the drape or the gloved hands of the clinician both of which must be maintained sterile. The outer surface of the drape is maintained sterile by the inward folding of the drape from the tabs 17, 18 (if present) toward the handles 14, 15. Furthermore, the hands of the clinician are on the opposite sides of the drape in order to remove the liners 16 which further ensures a sterile outer surface. Finally, since the drape is applied in a progressive manner (as opposed to current drapes which have the liner completely removed and the entire drape unfolded before application) less air is trapped beneath the drape and less wrinkling of the drape occurs. Therefore, often no effort is required to smooth out the drape post application which can compromise the sterility of the outer surface. As previously described, the gloved hands of the clinician are maintained sterile by providing handles that are sufficiently long to prevent contact with the surface of the skin.

The film 21 of the incise drape is formed from a transparent or translucent polymeric material which preferably allows for moisture evaporation through the film during prolonged surgeries. Suitable materials include polyolefins, such as low density polyethylene, polyurethanes such as polyester or polyether polyurethanes, (e.g., "Estane®" thermoplastic polyurethane," commercially available from B. F. Goodrich, Cleveland, Ohio, USA), polyesters such as polyether polyester (e.g., "Hytrel® polyester elastomer," commercially available from DuPont Co., Wilmington, Del., USA), and polyamides such as polyether polyamides (e.g., "Pebax®" Resins" commercially available from ELF Atochem, North America, Inc., Philadelphia, Pa., USA).

Furthermore, the film is preferably somewhat elastomeric to improve conformability. For these reasons, the preferred films are polyurethanes, polyether polyesters, and polyether polyamides. The film will typically have a thickness of less than 200 microns, preferably between about 6 to 130 microns, and most preferably between about 13 and 52 microns.

The release liners could be made of a variety of materials such as paper, plastic film, woven, non-woven, or knit textiles, as well as film textile laminates. The liner may be hydrophilic to allow fluid absorbency or may be hydrophobic without absorbency. Preferred release liner materials include polyethylene, paper, polypropylene, or polyester with a release coating of silicone, fluoro-chemical containing, or long chain alkyl containing material, or something which will allow the liner to be peeled away from the adhesive with a force of less than about 120, preferably less than 80 and most preferably less than 40 g/cm when measured in 1800 peel at speed of 225 cm per minute. A preferred release coating is "GE Silicone SS4331 Low Temperature, Fast Cure Paper Premium Release Coating" available from General Electric Company, Waterford, N.Y., USA. The amount of the release coating will vary depending on the level of adhesion and coating thickness of the adhesive layer.

The adhesive on the film is preferably a tacky pressure sensitive adhesive at room temperature which will adhere aggressively to the skin. Uniform attachment to the skin surface helps maintain a sterile surgical field. Aggressive adhesives are preferred due to the stress the incise drape is under during surgery as a result of the retraction of the wound, the warm moist environment, and the abrasion the drape may encounter as the surgeon's hands and instruments move in and out of the wound.

Suitable adhesives include acrylic adhesives, rubber based adhesives such as those based on natural rubber, polyisobutylene, butylene rubbers and the like, polyurethane type adhesives, and polyvinylethyl ether and copolymers or blends of these. Preferably the adhesive also contains an antimicrobial such as iodine, triiodide complexes, lactam-triiodide complexes such as povidone-iodine, chlorhexidine salts such as chlorhexidine gluconate and chlorhexidine acetate, hexachlorophene, parachlorometaxylenol (PCMX), phenols, Lauricidin (glycerol monolaurate), quaternary surfactants, silver, and silver salts such as silver chloride, silver oxide and silver, hydrogen peroxide and the like. The adhesive is preferably one of those described in U.S. Pat. Nos. 4,323,557; 4,931,282; 4,701,509; 4,732,808; 5,156,911; 5,017,625; and 5,204,110, incorporated herein by reference. The adhesive may be a continuous coating or may be pattern coated as described in U.S. Pat. Nos. 4,798,201 and 5,290,615, incorporated herein by reference. These adhesive types might also include various chemical modifiers e.g., tackifiers, crosslinkers, stabilizers, initiators, etc. to improve physical properties such as stability, viscosity, adhesion and the like.

Figure 23A:
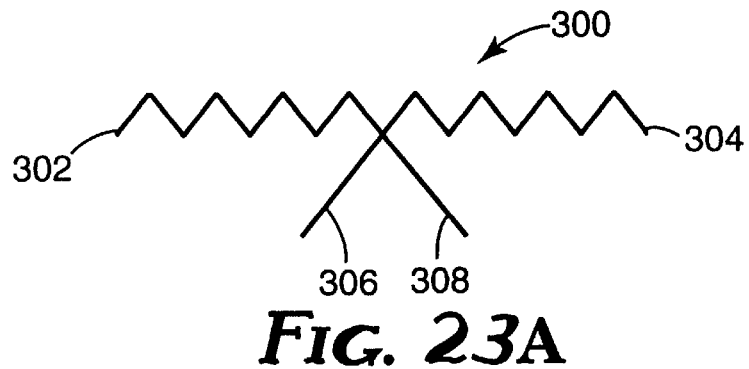
FIGS. 23A–D illustrate a preferred method of folding a surgical incise drape of the invention.
Figure 23B:
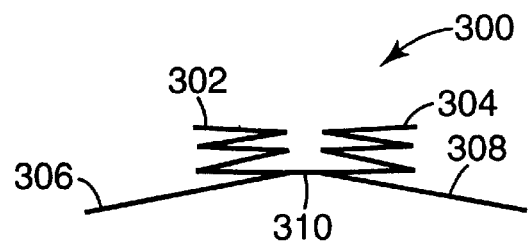
Figure 23C:
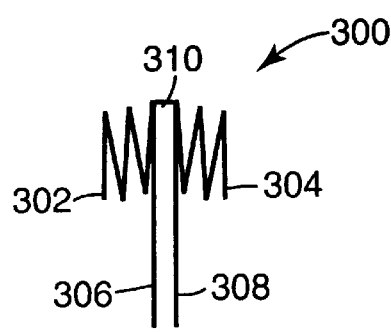
Figure 23D:
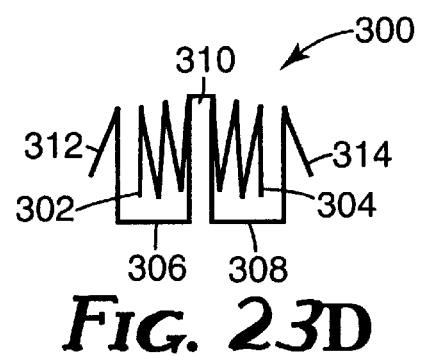

FIGS. 23A–D illustrate an alternative method of folding the drape 300 of the invention. As illustrated in FIG. 23A, the drape 300 is first fan-folded inwardly form opposite side edges 302 and 304 of the drape 300 toward the handles 306 and 308 to form a plurality of pleats defined by creased fold lines. The handles 306 and 308 are then folded back upon each other as illustrated by the changes between FIGS. 23A–23C, which helps to protect an otherwise exposed adhesive contact area 310. The handles 306 and 308 are then folded over the fan-folded portion of the drape 300 to help protect the drape 300, with any excess portion 312, 314 of the handles 306 and 308 then folded back over the handles 306, 308, as illustrated in FIG. 23D.

Figure 24:
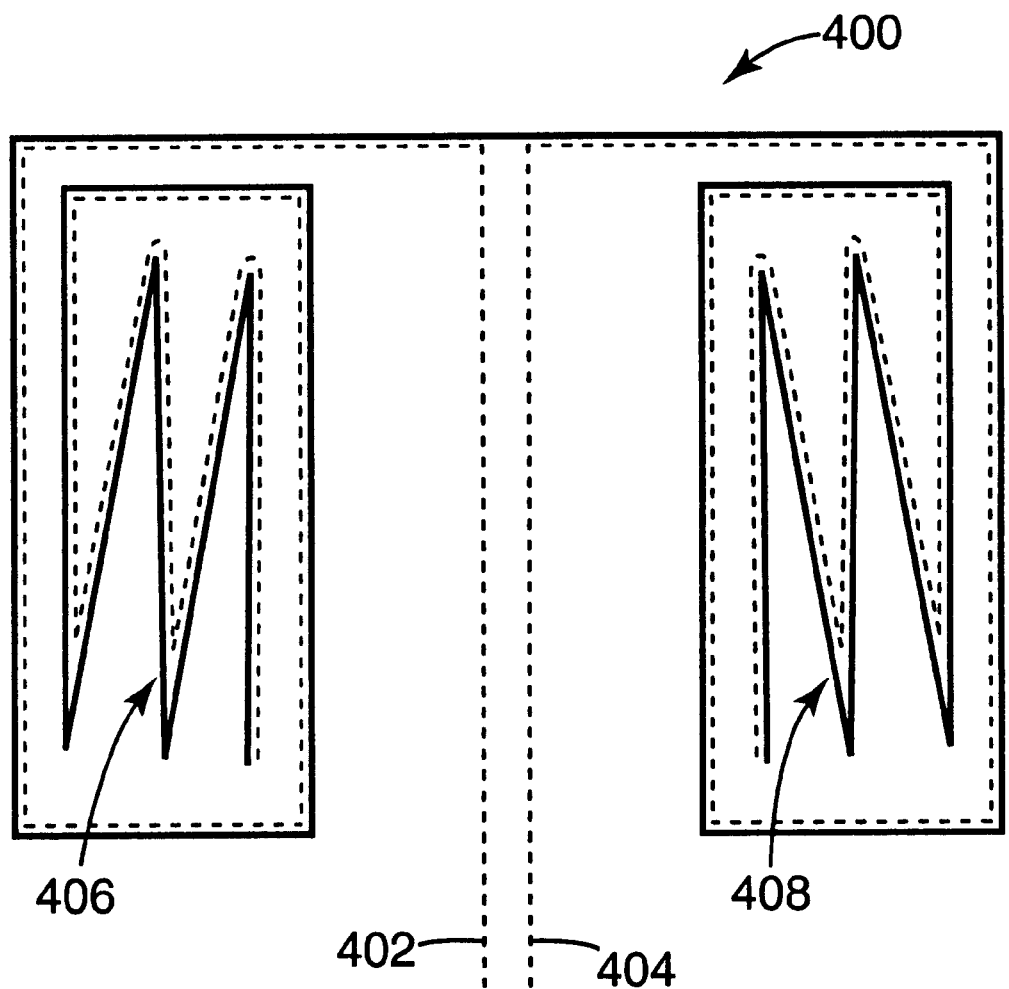
FIG. 24 is a schematic view of an alternative embodiment illustrating a hybrid method of fan-folding and rolling drape portions.

FIG. 24 illustrates an alternative method of folding the drape 400 of the invention, in which the drape 400 is first fan-folded inwardly from its opposite side edges toward the handles 402 and 404 to form fan-folded stacks 406 and 408, and the fan-folded stacks 406 and 408 are then rolled inwardly toward the handles 402 and 404. The fan-folded, rolled stacks are preferably flattened, with creases being formed along the fold lines of the fan-folded stacks 406 and 408.

The adhesive layer can be applied to the film according to any of various different conventional techniques, including co-extruding the film with the adhesive to form film and adhesive layers, coating the film with adhesive, or applying adhesive to the release liner so that the adhesive is transferred to the film.

Co-assigned U.S. patent application Ser. No. 08/857,724, filed May 16, 1997, by John Bruno, Patricia A. Eull and Matthew T. Scholz (Attorney Docket Number 53238USA8A), discloses a surgical incise drape with liner for providing tension, and is incorporated herein by reference.

The patents, patent documents, and publications cited herein are incorporated by reference in their entirety, as if each were individually incorporated by reference. Various modifications and alterations of this invention will become apparent to those skilled in the art without departing from the scope of the invention, and it should be understood that this invention is not to be unduly limited to the illustrative embodiments and methods set forth herein.

We claim:

1. A surgical incise drape comprising:
   a substantially transparent flexible film having opposite first and second major surfaces and opposite first and second side edges;
   a pressure sensitive adhesive on the first major surface of the film;
   a first liner comprising:
      a first handle spaced from the first side edge of the film; and
      a body portion attached to the first handle and removably covering at least a portion of the adhesive, the body portion extending along the adhesive from the first handle towards the first side edge;
   a second liner comprising:
      a second handle spaced from the second side edge of the film; and
      a body portion attached to the second handle and removably covering at least a portion of the adhesive, the body portion extending along the adhesive from the second handle towards the second side edge;
   a first plurality of folds in the drape between the first side edge and the first handle; and
   a second plurality of folds in the drape between the second side edge and the second handle;
   wherein the drape may be unfolded and the adhesive exposed by pulling the first and second handles apart.

2. The surgical incise drape of claim 1 wherein the the first plurality of folds is formed by repeatedly folded over by rolling the drape inwardly from the first side edge, and further wherein the second plurality of folds is formed by repeatedly folded over by rolling the drape inwardly from the second side edge.

3. The surgical incise drape of claim 1 wherein the first plurality of folds comprises a plurality of fan-folds between the first side edge and the first handle, and further wherein the second plurality of folds comprises a plurality of fan folds between the second side edge and the second handle.

4. The surgical incise drape of claim 1 wherein the distance between the first side edge of the film and the first handle is substantially equal to the distance between the second side edge of the film and the second handle.

5. The surgical incise drape of claim 1 wherein the distance between the first side edge of the film and the first handle differs from the distance between the second side edge of the film and the second handle by no more than 100 percent.

6. The surgical incise drape of claim 1 further comprising a central liner located between the first and second liners, the central liner covering at least a portion of the adhesive located between the first and second liners.

7. The surgical incise drape of claim 1 wherein the first and second liners are attached to the film adjacent the respective first and second side edges thereof such that the first and second liners remain attached to the respective first and second side edges of the film after the body portions of the first and second liners are removed from the adhesive.

8. The surgical incise drape of claim 7 wherein the first and second liners are attached to the film adjacent the respective first and second side edges thereof, and further wherein each of the first and second liners further comprises an adhesive portion that allows each of the first and second liners to be re-attached elsewhere after removal from the film.

9. The surgical incise drape of claim 8 further comprising at least one surgical attachment positioned upon at least one of the first and second liners.

10. The surgical incise drape of claim 9, wherein the at least one surgical attachment comprises a pouch.

11. The surgical incise drape of claim 1 further comprising at least one tab located along one of the first and second side edges of the film, the tab being substantially free of adhesive to facilitate manually grasping of the tab to remove the film from the patient.

12. The surgical incise drape of claim 1, wherein the first and second handles are at least 5 cm in width to facilitate aseptic removal of the first and second liners from the film.

13. The surgical incise drape of claim 1 further comprising a low adhesion backsize applied to at least a portion of the film on the major surface opposite the adhesive.

14. The surgical incise drape of claim 1, wherein the first and second liners are formed of flexible polymeric film material, the first and second liners being creased to keep the drape folded until the first and second liners are peeled from the transparent flexible film.

15. The surgical incise drape of claim 1, wherein the first handle comprises a first stiffening strip and the second handle comprises a second stiffening strip.

16. The surgical incise drape of claim 15, wherein the first stiffening strip is integral with the first handle and the second stiffening strip is integral with the second handle.

17. The surgical incise drape of claim 15, further comprising stiffening strip adhesive between the first stiffening strip and the first handle and between the second stiffening strip and the second handle.

18. The surgical incise drape of claim 17, wherein the stiffening strip adhesive remains attached to the first and second handles after the first and second stiffening strips are removed from the first and second handles.

19. The surgical incise drape of claim 1, further comprising a tab proximate at least one side edge of the film.

20. The surgical incise drape of claim 19, wherein the tab is substantially free of the adhesive on the first major surface of the film.

21. The surgical incise drape of claim 1, further comprising a first tab proximate the first side edge of the film and a second tab proximate the second side edge of the film.

22. The surgical incise drape of claim 21, wherein the first and second tabs are substantially free of the adhesive on the first major surface of the film.

23. The surgical incise drape of claim 1, wherein the film, the adhesive and the liner are capable of maintaining the first and second pluralities of folds.

24. The surgical incise drape of claim 2, wherein the first and second pluralities of folds are formed by rolling the drape such that the body portions of the first and second liners are outside and the film is on the inside of each of the rolls.

25. The surgical incise drape of claim 6, wherein the portion of the adhesive covered by the central liner is less than the portions of the adhesive covered by either of the body portions of the first and second liners.

26. A surgical incise drape comprising:

a substantially transparent flexible film having first and second major surfaces and first and second side edges;

a pressure sensitive adhesive on the first major surface of the film;

a first liner comprising:
  a first handle spaced from the first side edge of the film; and
  a body portion attached to the first handle and removably covering at least a portion of the adhesive, the body portion extending along the adhesive from the first handle towards the first side edge;

a second liner comprising:
  a second handle spaced from the second side edge of the film; and
  a body portion attached to the second handle and removably covering at least a portion of the adhesive, the body portion extending along the adhesive from the second handle towards the second side edge;

a first fold in the film along a line formed at a junction between the first and second liners, wherein the film is folded back on itself along the first fold; and a plurality of folds in the film, the body of the first liner, and the body of the second liner, the plurality of folds forming a stack in which the first and second side edges of the film are at a center of the stack;

wherein the drape may be unfolded and the adhesive exposed by pulling the first and second handles apart.

27. The surgical incise drape of claim 26, wherein the distance between the first side edge of the film and the first handle is substantially equal to the distance between the second side edge of the film and the second handle.

28. The surgical incise drape of claim 27, wherein the first and second liners are attached to the film adjacent the respective first and second side edges thereof such that the first and second liners remain attached to the respective first and second side edges of the film after the body portions of the first and second liners are removed from the adhesive.

29. The surgical incise drape of claim 28, wherein the first and second liners are attached to the film adjacent the respective first and second side edges thereof, and further wherein each of the first and second liners further comprises an adhesive portion that allows each of the first and second liners to be re-attached elsewhere after removal from the film.

30. The surgical incise drape of claim 29, further comprising at least one surgical attachment positioned upon at least one of the first and second liners.

31. The surgical incise drape of claim 30, wherein the at least one surgical attachment comprises a pouch.

32. The surgical incise drape of claim 26, wherein the first and second handles are at least 5 cm in width to facilitate aseptic removal of the first and second liners from the film.

33. The surgical incise drape of claim 26, further comprising a low adhesion backsize applied to at least a portion of the film on the major surface opposite the adhesive.

34. The surgical incise drape of claim 26, wherein the first and second liners are formed of flexible polymeric film material, the first and second liners being creased to keep the drape folded until the first and second liners are peeled from the transparent flexible film.

35. The surgical incise drape of claim 26, further comprising a tab proximate at least one side edge of the film.

36. The surgical incise drape of claim 35, wherein the tab is substantially free of the adhesive on the first major surface of the film.

37. The surgical incise drape of claim 26, further comprising a first tab proximate the first side edge of the film and a second tab proximate the second side edge of the film.

38. The surgical incise drape of claim 37, wherein the first and second tabs are substantially free of the adhesive on the first major surface of the film.

39. The surgical incise drape of claim 26, wherein the first handle comprises a first stiffening strip and the second handle comprises a second stiffening strip.

40. The surgical incise drape of claim 39, wherein the first stiffening strip is integral with the first handle and the second stiffening strip is integral with the second handle.

41. The surgical incise drape of claim 39 further comprising stiffening strip adhesive between the first stiffening strip and the first handle and between the second stiffening strip and the second handle.

42. The surgical incise drape of claim 41, wherein the stiffening strip adhesive remains attached to the first and second handles after the first and second stiffening strips are removed from the first and second handles.

* * * * *